US009063520B2

(12) United States Patent
Mann (10) Patent No.: US 9,063,520 B2
(45) Date of Patent: Jun. 23, 2015

(54) APPARATUS FOR INSERTING DELAY, NUCLEAR MEDICINE IMAGING APPARATUS, METHOD FOR INSERTING DELAY, AND METHOD OF CALIBRATION (71) Applicants: Kabushiki Kaisha Toshiba, Tokyo (JP); Toshiba Medical Systems Corporation, Tochigi (JP)

(72) Inventor: Gregory J. Mann, Oak Park, IL (US)

(73) Assignees: Kabushiki Kaisha Toshiba, Tokyo (JP); Toshiba Medical Systems Corporation, Tochigi (JP)

( * ) Notice: Subject to any disclaimer, the term of this patent is extended or adjusted under 35 U.S.C. 154(b) by 0 days.

(21) Appl. No.: 14/336,995

(22) Filed: Jul. 21, 2014

(65) Prior Publication Data
US 2014/0330117 A1  Nov. 6, 2014

Related U.S. Application Data (63) Continuation-in-part of application No. 13/841,364, filed on Mar. 15, 2013, now Pat. No. 8,786,474.

(51) Int. Cl.
*H03M 1/10* (2006.01)
*G04F 10/00* (2006.01)
(Continued)

(52) U.S. Cl.
CPC ............... *G04F 10/005* (2013.01); *H03L 5/00* (2013.01); *H03M 1/1009* (2013.01); *G01T 1/2985* (2013.01); *A61B 6/4417* (2013.01)

(58) Field of Classification Search
CPC ......... H03M 1/14; H03M 1/10; H03M 1/365; H03M 1/1245; H04H 20/67; H04N 5/378; H03L 7/18; H03L 7/085; H03L 7/089; H03L 7/1976; G06J 1/00; H03K 7/08; G06F 1/025; G02F 1/323; G02F 1/1347; G04F 10/06; G04F 10/005; G11C 11/4094; G11C 7/12; G11C 7/14; G11C 7/109; G11C 7/1075; G11C 7/1009; G11C 7/1078; G11C 7/1093; G11C 7/1045; G11C 7/1066
USPC .................. 341/110, 120, 155, 166; 375/362; 345/87, 90, 98, 102; 455/103, 501, 455/503; 250/362, 361 R; 368/113, 120
See application file for complete search history.

(56) References Cited

U.S. PATENT DOCUMENTS 6,741,505 B2 * 5/2004 Yokozeki ................. 365/189.15
7,564,284 B2    7/2009 Henzler et al.
(Continued)

OTHER PUBLICATIONS

International Search Report and Written Opinion issued Dec. 2, 2014 in PCT/IB2014/001176.

*Primary Examiner* — Lam T Mai
(74) *Attorney, Agent, or Firm* — Oblon, McClelland, Maier & Neustadt, L.L.P.

(57) ABSTRACT

An apparatus for inserting delay according to an embodiment includes a signal generating circuit, a plurality of carry elements, and a delay chain circuit. The delay chain circuit includes one or more delay modules selected from the plurality of carry elements, at least one feedback line connected between at least one of the delay modules and the signal generating circuit, and a plurality of enable inputs. Each of the plurality of enable inputs is provided in a respective one of the delay modules. The delay chain circuit is configured to generate an amount of delay based on a delay selection signal that is received at the enable inputs and that selects the amount of delay, and is configured to provide the selected amount of delay to the signal generating circuit, which is configured to incorporate the delay into the start signal.

10 Claims, 8 Drawing Sheets (51) Int. Cl.
  *H03L 5/00* (2006.01)
  *G01T 1/29* (2006.01)
  *A61B 6/00* (2006.01)

(56) References Cited

U.S. PATENT DOCUMENTS

| | | | |
|---|---|---|---|
| 7,663,946 B2 * | 2/2010 | Kim | 365/194 |
| 7,750,305 B2 | 7/2010 | Solf et al. | |
| 7,973,749 B2 * | 7/2011 | Uehara et al. | 345/87 |
| 7,986,256 B2 * | 7/2011 | Yamamoto et al. | 341/155 |
| 8,022,849 B2 * | 9/2011 | Zhang et al. | 341/142 |
| 8,159,286 B2 | 4/2012 | Rao et al. | |
| 8,164,493 B2 * | 4/2012 | Hsieh | 341/110 |
| 8,174,293 B2 | 5/2012 | Yoshihara et al. | |
| 8,222,607 B2 * | 7/2012 | Mann | 250/362 |
| 8,456,554 B2 * | 6/2013 | Takahashi | 348/294 |
| 8,531,322 B2 * | 9/2013 | Cao et al. | 341/111 |
| 8,786,474 B1 * | 7/2014 | Mann | 341/120 |
| 2010/0260242 A1 | 10/2010 | Abe et al. | |

* cited by examiner

APPARATUS FOR INSERTING DELAY, NUCLEAR MEDICINE IMAGING APPARATUS, METHOD FOR INSERTING DELAY, AND METHOD OF CALIBRATION

CROSS-REFERENCE TO RELATED APPLICATIONS

This application is a continuation-in-part application of, and claims the benefit of priority under 35 U.S.C. §120 from, U.S. application Ser. No. 13/841,364, filed Mar. 15, 2013, herein incorporated by reference. This application also claims the benefit of priority from prior International Application No. PCT/IB2014/001176, filed Mar. 13, 2014, herein incorporated by reference. A more complete appreciation of the embodiments described herein, and many of the attendant advantages thereof will be readily obtained as the same becomes better understood by reference to the following detailed description when considered in connection with the accompanying drawings. The embodiments described herein generally relate to a delay circuit for a metastable ring oscillator time-to-digital circuit (TDC) device and a related technique for improving measurement accuracy and resolution. The present application is related to U.S. Pat. No. 8,222,607, and the content thereof is incorporated herein by reference.

FIELD

Embodiments described herein relate generally to an apparatus for inserting delay, a nuclear medicine imaging apparatus, a method for inserting delay, and a method of calibration.

BACKGROUND

A time-to-digital-converter (TDC) is often used to measure timing in a gamma ray detector (detector). A TDC accurately converts the realization of an event into a number than can be related to the time the event occurred. Various methods exist to perform this task. Among others, counting a large number of very fast logic transitions between coarse clock cycles has been used to perform this task. In some cases, it may be desirable to indicate the occurrence of a series of events known to be generated sequentially. For instance, the time a rising signal takes to reach a pre-determined set of threshold values can be very useful information.

Time-to-digital converters have also been implemented with a variety of architectures, such as a classic delay chain having a single chain of identical delay elements connected in series or a Vernier delay chain.

An essential component of time-of-flight positron emission tomography (PET) systems is the time-to-digital converters that are used to measure the arrival time of detected photons at the detector. The measured time can be used to create a bound on the line-of-response, which can be used to estimate the position at which the positron emission event took place. As the accuracy of the TDC increases the bound becomes tighter, providing more accurate position information.

The accuracy of the delay-chain-based TDC is dependent upon the size in time of the sampled steps of the delay chain. In delay-chain TDCs, the sampled steps can vary by a significant amount depending upon the physical limitations of a circuit. In some cases variations of up to ten times have been observed.

While coarse offsets can be designed into the TDC and utilized to improve timing accuracy over single-edge delay chain based TDCs, there exists significant manufacturing-based variation in the speed of on-chip circuits. These variations will affect the optimal delay between edges that should be used to extract the maximal accuracy from the collective TDC circuit. Thus, there is a need to compensate for the manufacturing variation so as to increase the timing accuracy of the implemented TDC on every chip.

DETAILED DESCRIPTION

The apparatus for inserting delay according to an embodiment is an apparatus for inserting delay into a start signal of a time-to-digital circuit (TDC), and includes a signal generating circuit, a plurality of carry elements, and a delay chain circuit. The signal generating circuit is configured to generate the start signal. The plurality of carry elements are connected as a chain, and each of the carry elements has an input to receive a stop signal. The delay chain circuit includes one or more delay modules selected from the plurality of carry elements, at least one feedback line connected between at least one of the delay modules and the signal generating circuit, and a plurality of enable inputs. Each of the plurality of enable inputs is provided in a respective one of the delay modules. The delay chain circuit is configured to generate an amount of delay based on a delay selection signal that is received at the enable inputs and that selects the amount of delay, and is configured to provide the selected amount of delay to the signal generating circuit, which is further configured to incorporate the delay into the start signal.

A more complete appreciation of the embodiments described herein, and many of the attendant advantages thereof will be readily obtained as the same becomes better understood by reference to the following detailed description when considered in connection with the accompanying drawings. The embodiments described herein generally relate to a delay circuit for a metastable ring oscillator time-to-digital circuit (TDC) device and a related technique for improving measurement accuracy and resolution. The present application is related to U.S. Pat. No. 8,222,607, and the content thereof is incorporated herein by reference.

In one embodiment, there is described an apparatus for inserting delay into a start signal of a metastable ring oscillator chain-based time-to-digital circuit (TDC). The apparatus for inserting delay includes a signal generating circuit that generates the start signal, a plurality of carry elements connected as a chain, each of the carry elements having an input to receive a stop signal, a delay chain circuit including one or more delay modules selected from the plurality of carry elements, at least one feedback line connected between at least one of the delay modules and the signal generating circuit, and a plurality of enable inputs each provided in a respective one of the delay modules. The delay chain circuit generates an amount of delay based on a delay selection signal that is received at the enable inputs and that selects the amount of delay. The delay chain circuit also provides the selected amount of delay to the signal generating circuit, which incorporates the delay into the start signal.

In one embodiment, there is also described an apparatus including: the signal generating circuit configured to generate the start signal of the time-to-digital circuit (TDC); the plurality of carry elements connected as a chain, each of the carry elements having an input to receive a stop signal; and the delay chain circuit including one or more delay modules selected from the plurality of carry elements, at least one feedback line connected between at least one of the delay modules and the signal generating circuit, and a plurality of enable inputs each provided in a respective one of the delay modules, wherein the delay chain circuit is configured to generate an amount of delay based on the delay selection signal that is received at the enable inputs and that selects the amount of delay, and is configured to provide the selected amount of delay to the signal generating circuit, which is further configured to incorporate the delay into the start signal.

According to another embodiment of the apparatus for inserting delay, the signal generating circuit incorporates the delay into the start signal between edges in the signal.

According to another embodiment of the apparatus for inserting delay, the apparatus further includes a time determining circuit that determines the time at which an event occurred based on state information transferred from each of the delay elements.

According to another embodiment of the apparatus for inserting delay, the delay selection signal provides an indication to each delay module whether the respective delay module is activated to generate delay.

According to another embodiment of the apparatus for inserting delay, the signal generating circuit includes at least one flip-flop.

According to another embodiment of the apparatus for inserting delay, each delay module includes at least one hardware based look up table (LUT).

According to another embodiment of the apparatus for inserting delay, each delay module includes at least one flip-flop.

According to another embodiment of the apparatus for inserting delay, the delay selection signal is determined by user input.

According to another embodiment of the apparatus for inserting delay, the delay selection signal is determined by an algorithm which determines the optimal propagation delay for the TDC.

In one embodiment, there is described a method for inserting delay into a start signal of a metastable ring oscillator chain-based time-to-digital circuit (TDC). The method for inserting delay includes the steps of receiving a delay selection signal indicating a determination of an amount of delay to incorporate into the start signal, activating one or more delay modules based on the delay selection signal, the one or more delay modules selected from a plurality of carry elements connected as a chain, generating delay by routing a delay signal through an activated one of the one or more delay modules, and transmitting the delay signal to a signal generating circuit configured to generate the start signal to incorporate the delay signal.

According to another embodiment of the method for inserting delay, the method for inserting delay further includes the steps of receiving the delay signal at the signal generating circuit, generating a start signal incorporating the delay signal into the start signal, transmitting the start signal generated by the generating to the plurality of carry elements connected as a chain, receiving a stop signal at each of the plurality of carry elements and transmitting state information for each of the carry elements to a time determining circuit that determines the time at which an event occurred based on the state information.

According to another embodiment of the method for inserting delay, the generating step further includes the step of generating delay by routing the delay signal through the activated one of the one or more delay modules and each delay module following the activated one of the one or more delay modules until the delay signal reaches a delay module designated as a final delay module.

According to another embodiment of the method for inserting delay, the final delay module has a feedback line connected thereto.

According to another embodiment of the method for inserting delay, the feedback line is connected to the signal generating circuit.

According to another embodiment of the method for inserting delay, the step of generating delaying further includes the step of generating delay by routing the start signal through a logic array block look-up table (LUT) of the activated one of the one or more delay modules.

In one embodiment, there is described a method of calibrating a metastable ring oscillator chain-based time-to-digital circuit (TDC). The method includes the steps of receiving a delay selection signal indicating a determination of an amount of delay to incorporate into the start signal, activating one or more delay modules based on the delay selection signal, the one or more delay modules selected from a plurality of carry elements connected as a chain, generating delay by routing a delay signal through an activated one of the one or more delay modules, transmitting the delay signal to a signal generating circuit of the TDC which is configured to generate the start signal to incorporate the delay signal, measuring performance of the TDC using the delay selection signal to obtain an evaluation value for the delay selection signal, repeating the receiving, activating, generating, transmitting, and measuring step for each possible delay selection signal to obtain a corresponding evaluation value for each possible delay selection signal, and determining which of the possible delay selection signals results in a highest evaluation value.

In general, time-to-digital converter (TDC) devices according to exemplary embodiments each include at least one delay chain circuit that generates a value corresponding to a time period corresponding to a start signal and a stop signal.

The present embodiments provide a calibration path for a TDC implemented as a metastable ring oscillator delay chain implemented on programmable logic devices e.g., Field Programmable Gate Arrays (FPGAs).

Metastable ring oscillators are used to generate multiple transitions on a signal, each of which has a fixed time relationship to the ring oscillator input. The accuracy of a delay chain-based TDC is dependent upon the size in time of the sampled steps of the delay chain. In FPGA-based implementations of delay chain TDCs, these sampled steps can vary by a significant amount. By utilizing a metastable ring oscillator, multiple edges can be propagated through the chain of a multi-hit TDC, and as one edge is measured in a large bin, a subsequent edge or edges can be measured in smaller bins.

The present embodiments provide a way by which TDCs implemented as a single multi-hit detectable delay chain with a triggerable metastable ring oscillator at the start of the chain on programmable logic devices (i.e. FPGAs), can be calibrated. Due to inherent differences in propagation delays for silicon devices caused by manufacturing variances, as well as non-uniformity in tap delays on the delay chain (e.g. intra-logic array block delays versus inter-logic array block delays on FPGAs), a fixed ring-oscillator period will not necessarily yield the optimal performance across different physical dies. The present embodiments provide a way by which the period of the metastable ring oscillator circuit can be modified. Thus, by adjusting the ring oscillator period, the time between propagated edges can be calibrated to provide the optimal spacing to provide compensation for structural non-linearity in the delay chain.

Figure 1:
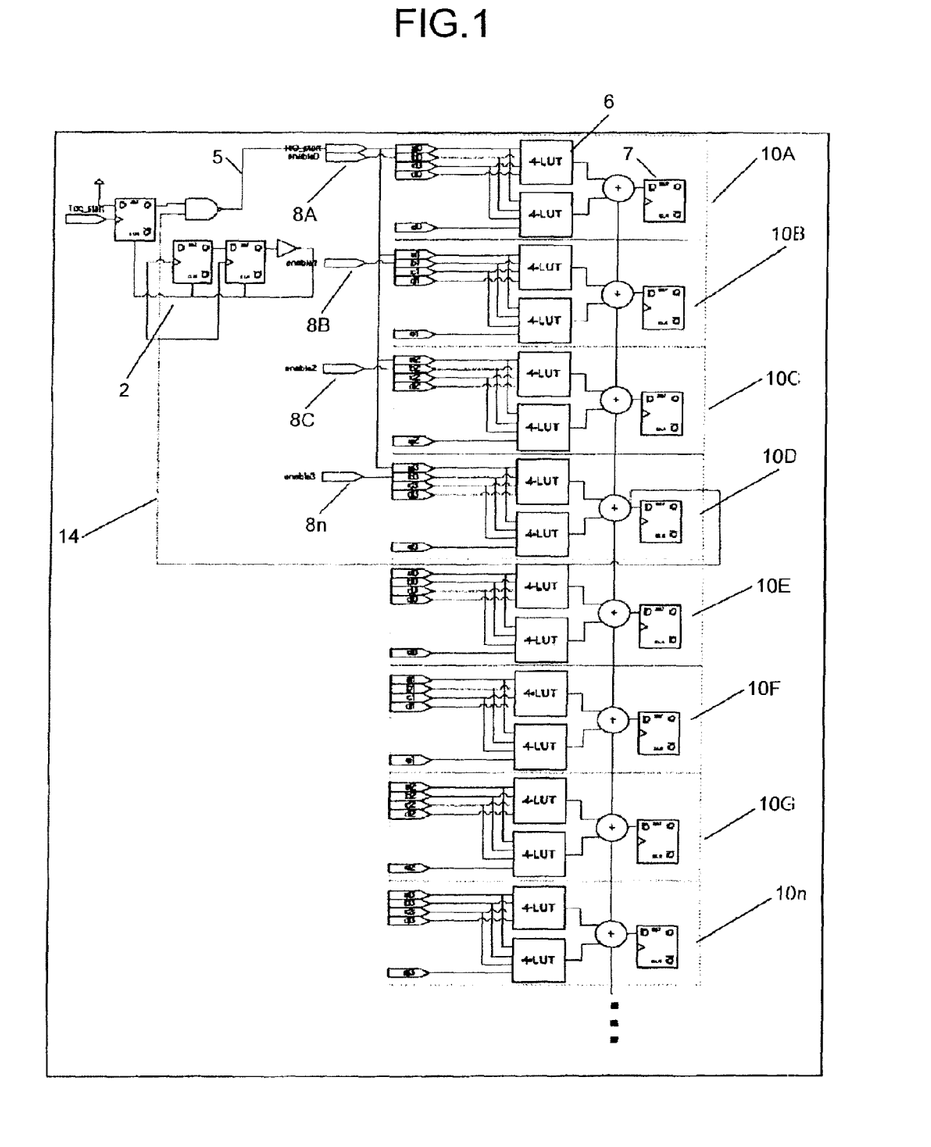
FIG. 1 is a schematic drawing of an apparatus for introducing propagation delay to a chain-based metastable ring oscillator time-to-digital circuit (TDC) according to one embodiment.

Referring now to the drawings, wherein like reference numerals designate identical or corresponding parts throughout the several views. FIG. 1 is a schematic drawing of an apparatus for introducing propagation delay to a chain-based metastable ring oscillator time-to-digital circuit (TDC) according to one embodiment. More specifically, FIG. 1 is a schematic drawing of a FPGA-based metastable ring oscillator time-to-digital circuit. This circuit can be used to both provide calibration paths for introducing delay into the oscillated signal and to implement the time-to-digital conversion.

As is illustrated in FIG. 1, a TDC chain is provided, which includes a number of fast-carry-chain elements 10A-n. Each fast-carry-chain element 10A-n includes at least one FPGA implemented n-bit look up table (LUT) 6, a standard full-adder circuit, and a logic element such as a D-type flip-flop 7. The flip flops implement the stop function of the TDC. The stop signal is the clock signal to the flip-flops. The metastable oscillator signal is generated by a signal generating circuit 2.

The fast-carry-chain elements 10A-n of FIG. 1 may be implemented with discrete logic gates, as an Application Specific Integrated Circuit (ASIC), a FPGA, or other Complex Programmable Logic Device (CPLD). In FPGA or CPLD implementations, the device may be coded in VHDL, Verilog or any other hardware description language as a set of computer-readable instructions, and the computer-readable instructions may be stored in electronic memory directly in the FPGA or CPLD, or as separate electronic memory. Further, the electronic memory may be non-volatile, such as a ROM, EPROM, EEPROM, or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

At least one of the fast-carry-chain elements 10A-n includes an enable signal 8A-n as input. The enable signal 8A-n is utilized for the introduction of a delay into the oscillated signal. Signal line 14 provides an example of a feedback line by which the delay is introduced. The feedback line 14 may be positioned on each or any of the fast-carry-chain elements 10A-n. Each fast-carry-chain element 10A-n can be used to introduce a specific or predetermined amount of delay into the signal.

Figure 2:
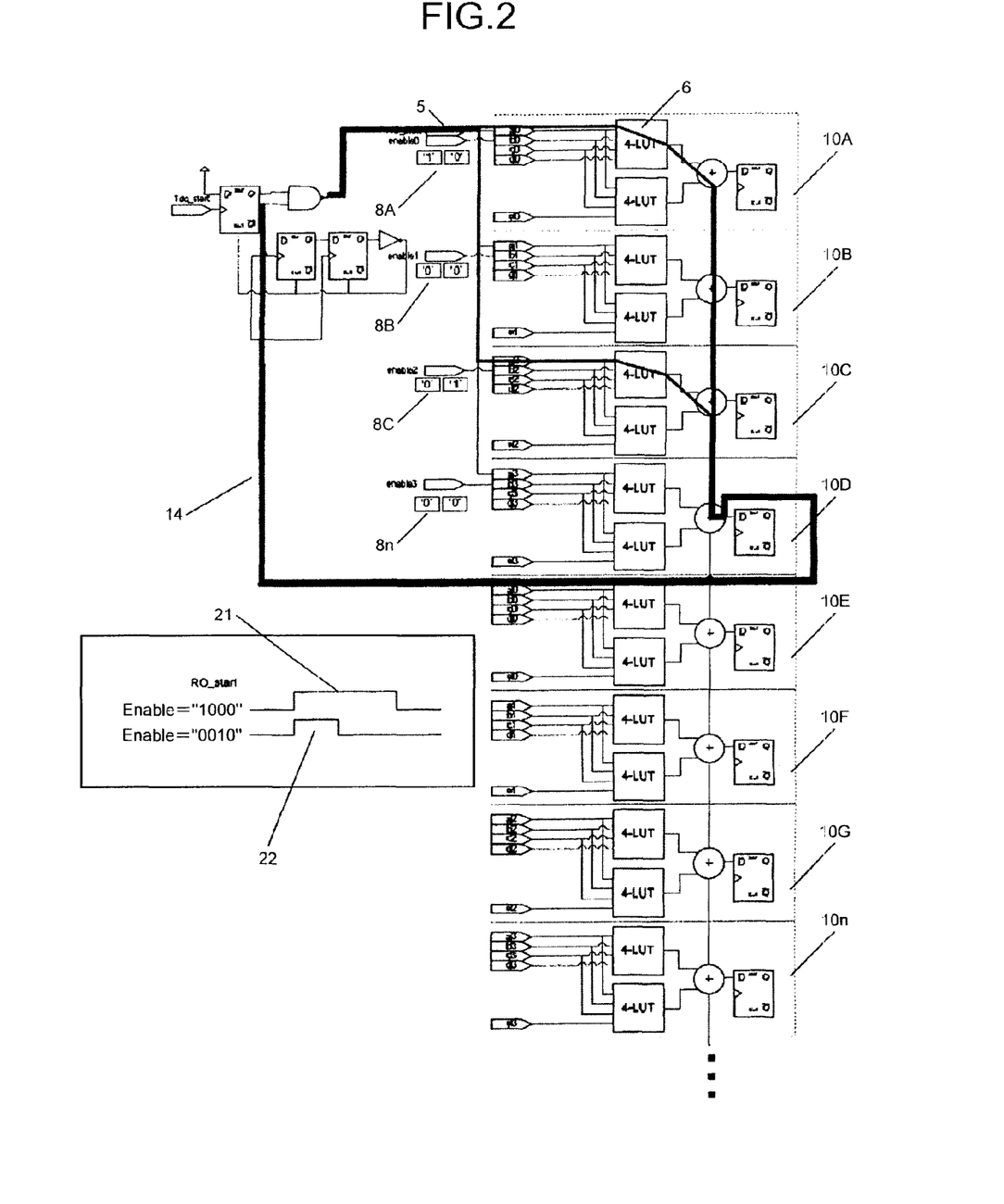
FIG. 2 is a schematic drawing illustrating the operation of the apparatus for introducing propagation delay to a chain-based metastable ring oscillator time-to-digital circuit (TDC) according to one embodiment.

As is shown in FIG. 2, the "RO_Start" signal input 5 is input to the beginning of the fast-carry-chain elements 10A-n. Each fast-carry-chain element 10A-n includes at least one FPGA LUT that is configured to pass the "RO_Start" signal through to the carryout output of the fast-carry-chain element when the respective enable signal 8A-n is asserted. With the enable signals 8A-n asserted in a one-hot fashion, each possible combination yields a different propagation delay from the "RO_Start" input to the ring oscillator feedback. Utilizing differing combinations of enable signal 8A-n assertions, a combination is obtained that provides the optimal timing accuracy performance for the TDC as a whole.

As is shown in FIG. 2, the enable signal "1000" indicates that the first fast-carry-chain element 10A is enabled. In the first example shown in FIG. 2, the signal then passes through fast-carry-chain elements 10A-10D providing a delay 21. In the second example associated with enable signal "0010", the third fast-carry-chain element 10C is enabled generating a smaller amount of delay 22. In these examples, the feedback line 14 is positioned at the fast-carry-chain element 10D. However, the feedback line 14 can be positioned at any or each of the fast-carry-chain elements 10A-n. In an alternate example, the first "1" in the enable signal indicates the input to the delay chain and the second "1" in the enable signal indicates the output of the delay chain. Thus, if the enable signal was "1001", the first fast-carry-chain element 10A would be activated as the input and the fast-carry-chain element 10D would be activated as the last element in the delay chain.

Applicants note that although a single ring oscillator chain is illustrated, more than one chain may be included in the system. In such an embodiment, the result from the different chains can be combined by way of, for example, averaging to arrive at the final time value at a microprocessor or other calculating circuit.

The FPGA-based implementation makes use of the fast-carry-chain architecture of FPGA devices. These fast-carry-chains are utilized as the delay taps in the delay chain used in the TDC. By routing the metastable ring oscillator output to multiple logic array block (LAB) look-up tables (LUTs) 6, separate enable signals 8A-n routed to the LUTs 6 can activate paths of different propagation delays to the feedback path 14 to the metastable ring oscillator, resulting in programmable delays between rising and falling edges of the metastable ring oscillator output.

The multiple logic array block (LAB) look up tables (LUTs) 6 shown in FIG. 2 may be implemented using FPGAs and are configured to pass the "RO_Start" signal 5 through the fast-carry-chain elements 10A-n, when the respective enable signal 8A-n is activated. By utilizing all possible combinations of enable 8A-n activations, a combination can be determined that provides the optimal timing accuracy performance of the TDC as a whole. The accuracy of the TDC circuit is measured by injecting pairs of start-stop signals of known timing (for example from a function generator). For each configuration of enable signal 8A-n as described above, a histogram of the times between the start and stop, as measured by the TDC in a given configuration, is generated. A distribution of timing values is derived from the histogram. The distribution is analyzed and the quality of the configuration is based on some metric calculated in the distribution. Examples of the metric include but are not limited to the standard deviation or the Full Width Half Max (FWHM).

These metrics measure the "width" of the distribution, where a smaller "width" is preferable.

The path used for propagation is known a priori due to dynamically changing the configuration. An external source (such as a predetermined software application) sets the configuration. Since the source is setting the configuration, the source knows the current configuration.

Figure 3:
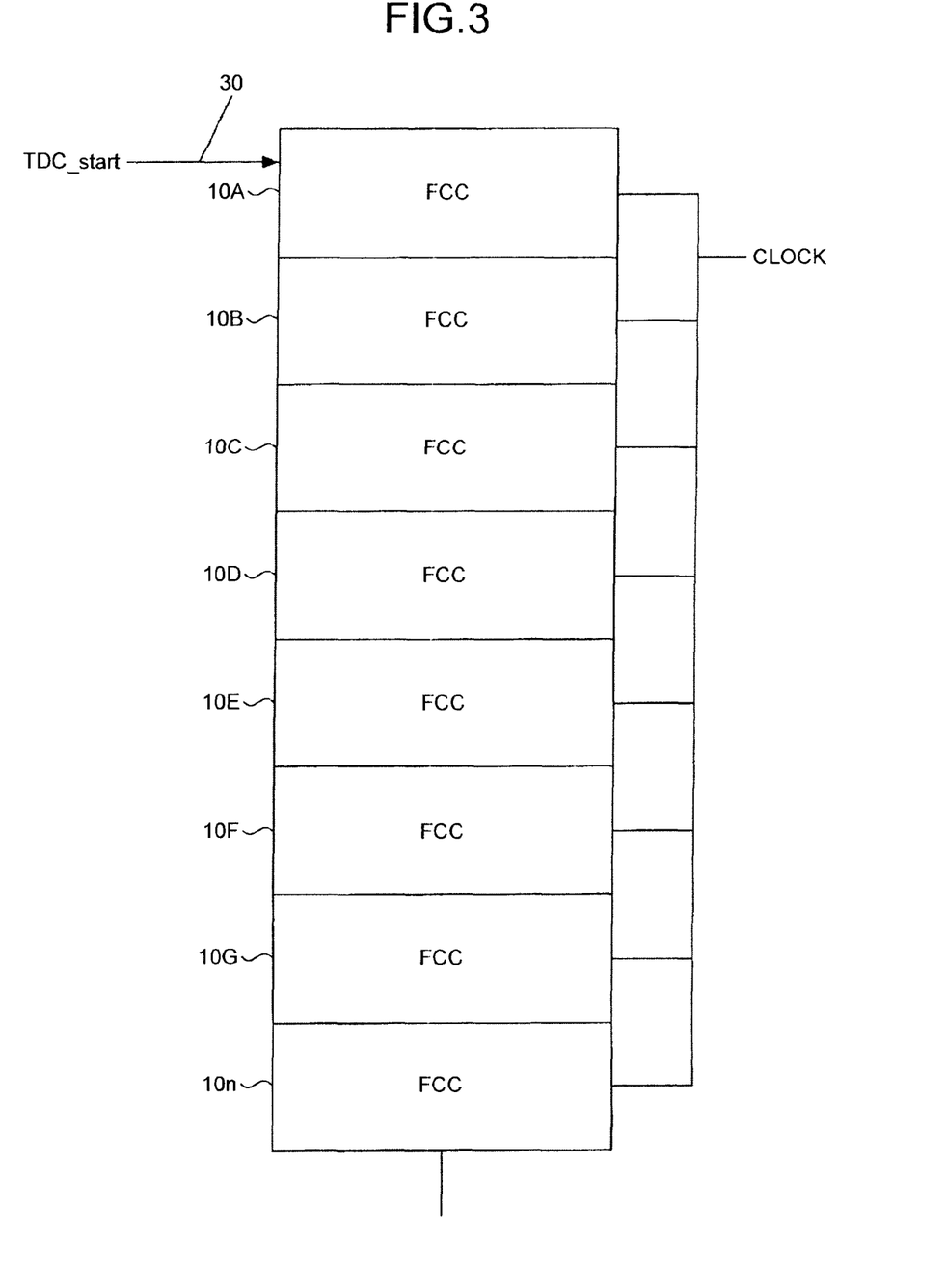
FIG. 3 is another schematic drawing of the apparatus for introducing propagation delay to a chain-based metastable ring oscillator time-to-digital circuit (TDC) according to one embodiment.

FIG. 3 is another schematic drawing of the apparatus for introducing propagation delay to the chain-based metastable ring oscillator time-to-digital circuit (TDC) according to one embodiment. More specifically, FIG. 3 illustrates a view of the system, which implements the time-to-digital conversion using the fast-carry-chain (FCC) elements 10A-n. As illustrated in the figure, the start signal TDC_start is received at input 30 having included therein delay generated by the delay process shown in FIG. 2. The metastable ring oscillator inputs the signal having multiple edges into the fast-carry-chain elements 10A-n. The stop signal is provided as the clock signal and "freezes" the state of fast-carry-chain elements at the moment the clock signal provides the stop signal. The states of each of the fast-carry-chain elements 10A-n is then output to a CPU or some other microprocessing device or circuit in order to determine the timing of the event. The CPU, microprocessing device or circuit implements a time determining circuit that determines the time at which an event occurred based on state information of each of the fast-carry-chain elements 10A-n.

The TDC chain described above may be, for example, implemented within a PET system. However, the above described TDC chain is not limited to use within a PET system. In such a time-of-flight PET system, a TDC chain typically produces a time stamp with an accuracy of in the range of ps.

A commercial gamma ray detector such as in a PET system includes an array of scintillator crystals coupled to a transparent light guide, which distributes scintillation light over an array of photomultiplier tubes (PMTS) arranged over the transparent light guide. Signals from the PMTS in a same area are generally summed in the analog domain, and then timing is measured based on the leading edge of the summed signal, or event.

Figure 4:
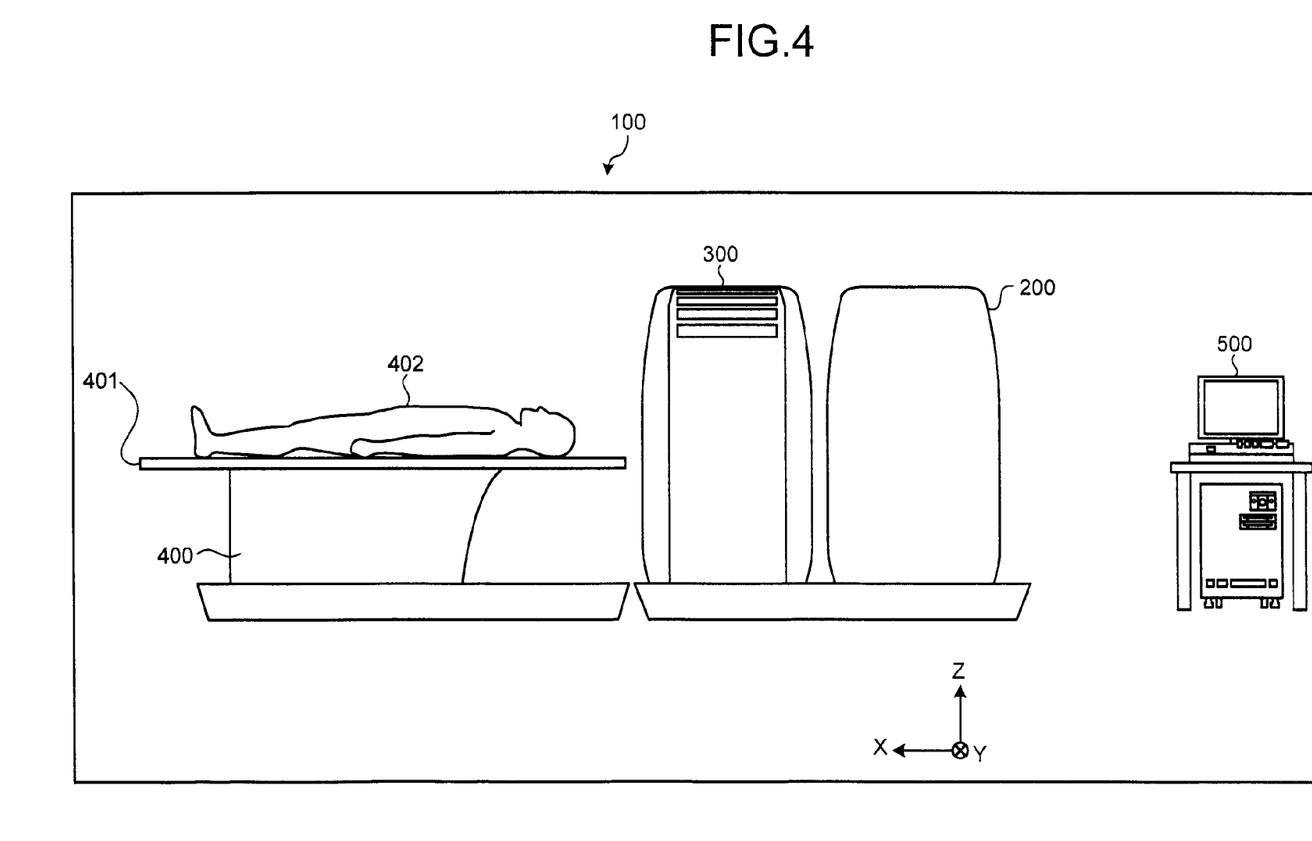
FIG. 4 is an explanatory drawing illustrating an example of a nuclear medicine imaging apparatus according to an embodiment.

FIG. 4 is an explanatory diagram illustrating an example of a nuclear medicine imaging apparatus. As is shown in FIG. 4, an example of the nuclear medicine imaging apparatus as the PET system includes a PET-CT apparatus 100. In FIG. 4, 200 denotes a PET scanner, 300 denotes an X-ray CT scanner, 400 denotes a bed, 401 denotes a tabletop on which a subject is lying, and 402 denotes the subject. The PET-CT apparatus 100 includes the PET scanner 200, the X-ray CT scanner 300, the bed 400, and a console device 500. The X-direction in FIG. 4 represents a direction of the body axis of the subject 402 lying on the tabletop 401 illustrated in FIG. 4. The Y-direction represents a direction orthogonal to the X-direction on a horizontal plane. The Z-direction represents a vertical direction.

The bed 400 includes the tabletop 401 on which the subject 402 is lying. Furthermore, the bed 400 includes a bed control unit, which is not illustrated in FIG. 4, for moving the tabletop 401. The bed control unit is controlled by the console device 500, and moves the subject 402 lying on the tabletop 401 into an imaging bore of the PET-CT apparatus 100.

The PET scanner 200 includes a plurality of photon counting gamma ray detectors (to be described later) that count light derived from gamma rays for reconstructing a PET image. The gamma ray detectors are arranged in a ring shape around the body axis of the subject 402. The gamma ray detectors, from outside of the body of the subject 402 lying on the tabletop 401, detect a pair of gamma rays (pair annihilation gamma rays) emitted from the inside of the body of the subject 402, for example.

Specifically, every time the gamma ray detectors count the gamma rays, the PET scanner 200 collects counting information including the detection position indicating the position of a gamma ray detector that detects the gamma rays, the energy value at the time when the gamma rays are incident on the gamma ray detector, and the detection time at which the gamma ray detector detects the gamma rays. The TDC described above is used in collecting the detection time. This causes the PET-CT apparatus 100 to reconstruct a PET image in which a path of the heavy particle beam is visualized.

The X-ray CT scanner 300 includes an X-ray tube that emits X-rays for reconstructing an X-ray CT image and an X-ray detector that detects the X-rays emitted by the X-ray tube. In the X-ray CT scanner 300, the X-ray tube irradiates the subject 402 with the X-rays, and the X-ray detector detects the X-rays passing through the subject 402. Specifically, the X-ray tube emits the X-rays, and the X-ray detector detects the X-rays while the X-ray CT scanner 300 is rotating about the body axis of the subject 402. In other words, the X-ray CT scanner 300 irradiates the subject with the X-rays in multi-directions, and detects the attenuated X-rays absorbed in the subject 402 by passing through the subject 402 while being rotating about the body axis of the subject 402. Data generated by performing amplification processing, AD conversion processing, and the like on the X-rays detected by the X-ray detector is also referred to as "X-ray projection data". The X-ray CT scanner 300 collects the X-ray projection data and the detection position at which the X-rays used for generating the X-ray projection data are detected.

Figure 5:
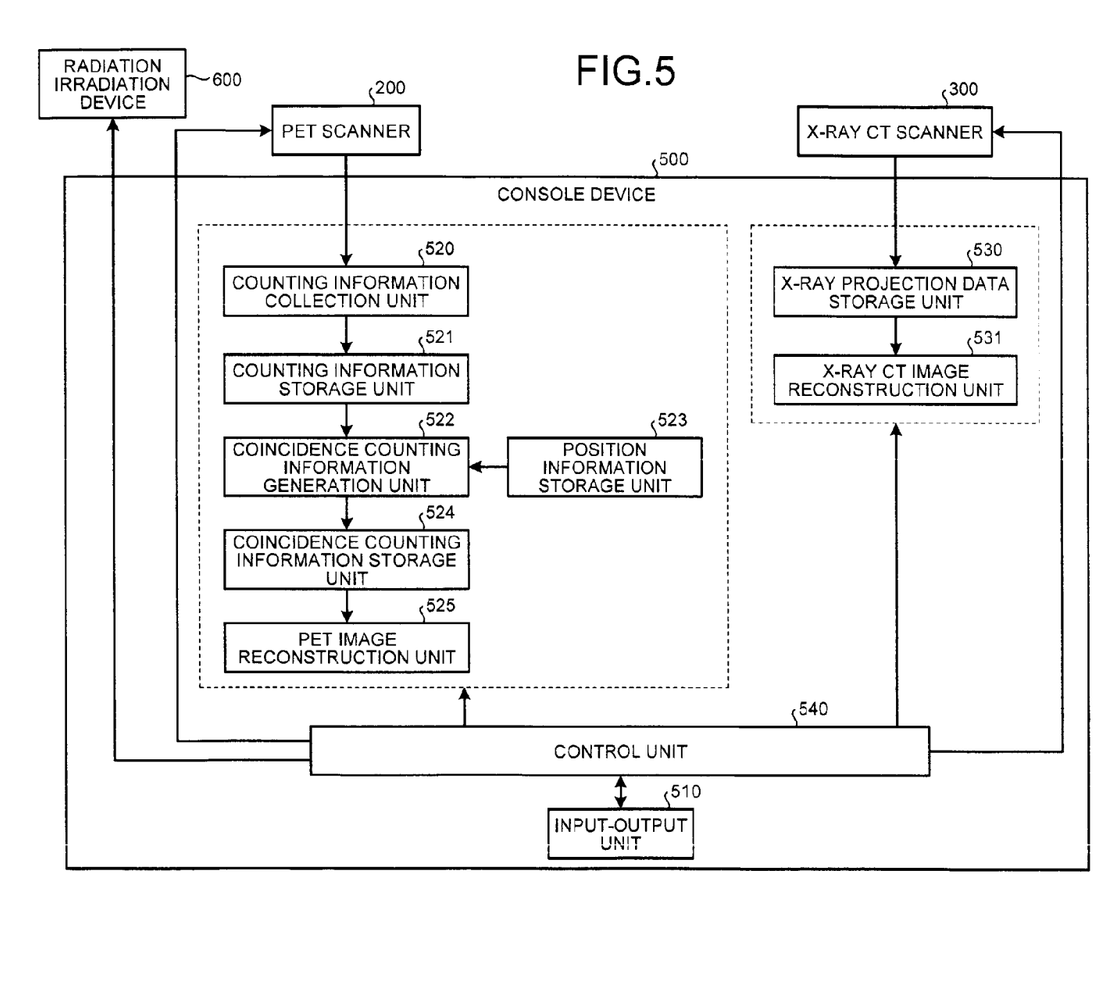
FIG. 5 is a block diagram illustrating an example of a configuration of a console device according to an embodiment.

FIG. 5 is a block diagram of an exemplary configuration of the console device according to the embodiment. The console device 500 reconstructs an X-ray CT image based on the information collected by the X-ray CT scanner 300. Furthermore, the console device 500 generates coincidence counting information by using the counting information collected by the PET scanner 200, and reconstructs a PET image based on the coincidence counting information thus generated. In the description below, the processing for reconstructing a PET image and the processing for reconstructing an X-ray CT image by the console device 500 may be performed by using an arbitrary method, and an explanation thereof will be made succinctly.

In the example illustrated in FIG. 5, the PET scanner 200, the X-ray CT scanner 300, and a radiation irradiation device 600 are illustrated in addition to the console device 500 as a matter of convenience for explanation. As shown in FIG. 5, the console device 500 includes an input-output unit 510 and an control unit 540. In addition, the console device 500 includes an X-ray projection data storage unit 530 and an X-ray CT image reconstruction unit 531 so as to reconstruct an X-ray CT image. Furthermore, the console device 500 includes a counting information collection unit 520, a counting information storage unit 521, a coincidence counting information generation unit 522, a position information storage unit 523, a coincidence counting information storage unit 524, and a PET image reconstruction unit 525 so as to reconstruct a PET image. In the embodiment, an explanation is made of the case where one console device 500 reconstructs an X-ray CT image and a PET image. However, the embodiment can be applied to the case where reconstruction of an X-ray CT image and reconstruction of a PET image are performed in different console devices.

The input-output unit 510 is connected to the control unit 540. The input-output unit 510 receives various types of instructions from a user who uses the radiation therapy apparatus, and transmits the various types of instructions thus received to the control unit 540. Furthermore, the input-output unit 510 receives information from the control unit 540, and outputs the information thus received to the user. The input-output unit 510 is, for example, a keyboard, a mouse, a microphone, a monitor, and a speaker. Explanations of details of the information and the instructions received by the input-output unit 510 and a detail of the information output by the input-output unit 510 are omitted herein.

The control unit 540 includes an internal memory that stores therein a program specifying various types of processing processes and the like, and controls various types of processing. For example, the control unit 540 is an electronic circuit, such as an ASIC, an FPGA, a CPU, and a micro processing unit (MPU). The control unit 540 controls the whole processing of the radiation therapy apparatus. Specifically, the control unit 540 controls the PET scanner 200 and the X-ray CT scanner 300, thereby controlling radiography performed by the PET-CT apparatus 100. Furthermore, the control unit 540 controls the radiation irradiation device 600 so as to emit the heavy particle beam in multi-directions consecutively or intermittently in accordance with the treatment plan.

The control unit 540 controls the reconstruction processing of a PET image and the reconstruction processing of an X-ray CT image in the console device 500. Furthermore, the control unit 540 displays a PET image, an X-ray CT image, a superimposed image of a PET image and an X-ray CT image, or the like on the monitor of the input-output unit 510.

The X-ray projection data storage unit 530 stores therein X-ray projection data transmitted from the X-ray CT scanner 300. The X-ray CT image reconstruction unit 531 performs back projection processing on the X-ray projection data stored in the X-ray projection data storage unit 530 by the filtered back projection (FBP) method, for example, thereby reconstructing an X-ray CT image.

The counting information collection unit 520 collects counting information from counting results output by an detectors 210, and stores the counting information in the counting information storage unit 521. In other words, in the counting information collection unit 520, the TDC described above is used in collecting the detection time included in the counting information. The counting information collection unit 520 sequentially receives the counting information collected by the PET scanner 200, and stores the counting information thus received in the counting information storage unit 521. The counting information collection unit 520 may be included in the PET scanner 200.

The counting information storage unit 521 stores therein the counting information stored by the counting information collection unit 520. For example, the counting information storage unit 521 is a semiconductor memory device, such as a RAM and a flash memory, or a storage device, such as a hard disk and an optical disk. The counting information storage unit 521 stores therein the "scintillator number", the "energy value", and the "detection time" in a manner corresponding to the "module ID". The "module ID" is the information uniquely identifying the detector provided in plurality.

The coincidence counting information generation unit 522 generates a combination of two pieces of counting information whose difference in detection time is within a time window among the counting information stored in the counting information storage unit 521 as coincidence counting information obtained by counting pair annihilation gamma rays nearly coincidentally.

Specifically, the coincidence counting information generation unit 522 generates the coincidence counting information based on conditions of coincidence counting information generation specified by an operator. The conditions of coincidence counting information generation include the time window, for example. The time window indicates an upper limit of difference between two detection times in the case where a pair of gamma rays are both counted.

For a pair of gamma rays emitted coincidentally from a positron-emitting radionuclide, the detection times of the gamma rays each included in the pair of gamma rays are the same, or difference between the two detection times is small even if the detection times are not the same. As a result, the coincidence counting information generation unit 522 uses the time window to prevent false coincidence counting information from being generated.

For example, an explanation will be made of the case where the coincidence counting information generation unit 522 generates the coincidence counting information by using a time window of "10 nanoseconds". In this case, the coincidence counting information generation unit 522 refers to the "detection time (T)" of each "module ID", and searches for a combination of the counting information whose difference between two detection times is within a "time window of 10 nanoseconds" among the modules.

Searching for a combination in which the detection time is within the time window is also referred to as "coincidence finding". A list of the coincidence counting information generated by the coincidence counting information generation unit 522 is also referred to as a "coincidence list".

An energy window may be set as the conditions of coincidence counting information generation. The energy value of a pair of gamma rays emitted by annihilation of a positron is already specified in advance. For example, 18F, 15O, and 11C each emit gamma rays of "511 keV". Therefore, any gamma rays emitted coincidentally from a positron-emitting radionuclide have an energy value within a predetermined range. As a result, the coincidence counting information generation unit 522 uses the energy window to exclude counting information not of the pair of gamma rays emitted from the positron-emitting radionuclide, and generates the coincidence counting information. Thus, the coincidence counting information generation unit 522 can prevent false coincidence counting information from being generated. As described above, setting the conditions of coincidence counting information generation makes it possible to perform random correction for excluding accidental coincidence counting, scatter correction for preventing counting information of scattered gamma rays from being generated as the coincidence counting information, sensitivity correction for correcting difference in sensitivity among the detectors, and other correction.

The coincidence counting information generation unit 522 then stores the coincidence counting information thus generated in the coincidence counting information storage unit 524. For example, the coincidence counting information storage unit 524 is a semiconductor memory device, such as a RAM and a flash memory, or a storage device, such as a hard disk and an optical disk.

The PET image reconstruction unit 525 reads the coincidence counting information generated by the coincidence counting information generation unit 522 from the coincidence counting information storage unit 524, and uses the coincidence counting information thus read to reconstruct a PET image. Specifically, the PET image reconstruction unit 525 considers the coincidence counting information to be projection data of the gamma rays, and reconstructs the PET image from the projection data of the gamma rays by using a successive approximation method. The successive approximation methods include a maximum likelihood expectation maximization (MLEM) method, and an ordered subset MLEM (OSEM) method in which the convergence time is significantly shortened by improving the algorithm of the MLEM method. The PET image reconstructed by the PET image reconstruction unit 525 is displayed on the monitor of the input-output unit 510 by control of the control unit 540.

For each PMT, there may be an independent electronics path that is used to measure the amplitude of the signal on each PMT. This path may include a filter and an analog-to-digital converter (ADC). The filter, typically a bandpass filter, is used to optimize the signal-to-noise ratio of the measurement and performs an anti-aliasing function prior to conversion to a digital signal by the ADC. The ADC can be a free-running type, running at 100 MHz, for example, in which case a central processing unit performs a digital integration, or the ADC can be a peak-sensing type. The ADC and TDC outputs are provided to the CPU for processing. The processing includes of estimating an energy and position from the ADC outputs, and an arrival time from the TDC output for each event, and may include the application of several correction steps, based on prior calibrations, to improve the accuracy of the energy, position, and time estimates.

As one of ordinary skill in the art would recognize, the CPU can be implemented as discrete logic gates, as an ASIC, a FPGA or other CPLD. An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the CPU may be implemented as a set of computer-readable instructions stored in any of the above-described electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor (registered trademark) from Intel of America or an Opteron processor (registered trademark) from AMD of America and an operating system, such as Microsoft VISTA (registered trademark), UNIX (registered trademark), Solaris (registered trademark), LINUX (registered trademark), Apple (registered trademark), MAC-OSX (registered trademark) and other operating systems known to those skilled in the art.

Once processed by the CPU, the processed signals are stored in electronic storage, and/or displayed on display. As one of ordinary skill in the art would recognize, electronic storage may be a hard disk drive, CD-ROM drive, DVD drive, FLASH drive, RAM, ROM or any other electronic storage known in the art. Display may be implemented as an LCD display, CRT display, plasma display, OLED, LED or any other display known in the art. As such, the descriptions of the electronic storage and the display provided herein are merely exemplary and in no way limit the scope of the present advancements.

The CPU can also, in an alternative embodiment, perform calculations to determine the best propagation delay for the TDC chain. Thus, the CPU can use feedback control or other similar mechanisms to determine how much propagation delay to add to the chain to increase the timing accuracy of the implemented TDC. In such an embodiment, the enable signals 8A-n are output by the CPU and input into the respective fast-carry-chain modules.

Figure 6A:
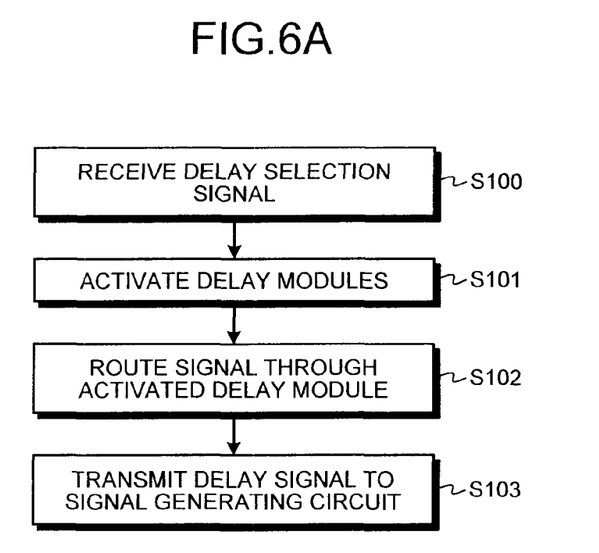
FIG. 6A is a flow diagram illustrating a process of inserting delay into a start signal of a metastable ring oscillator chain-based time-to-digital circuit (TDC).

FIG. 6A illustrates a method inserting delay into a start signal of a metastable ring oscillator chain-based TDC. For example, the processing in the flowchart is performed controlled by the control unit 540 (see FIG. 5) or a main processing unit 1004 (see FIG. 8).

In step S100, a delay selection signal, corresponding to enable signals 8A-n, is received indicating a determination of an amount of delay to incorporate into the start signal.

In step S101, one or more delay modules is activated based on the delay selection signal, the one or more delay modules selected from the chain of fast-chain-carry elements 10A-n.

In step S102, delay is generated by routing a delay signal through at least one of the one or more delay modules that has been activated by the delay selection signal. As is described above, the activated delay module may be determined to be the delay module into which the delay signal is first introduced. Therefore, if the delay signal is introduced into a delay module further down the chain from the first module 10A, for example, if the signal is introduced into the third fast-carry-chain element 100 as is shown in the example illustrated in FIG. 2, the delay that results from the delay process is less (see delay 22 as compared with delay 21).

In step S103, the delay signal is transmitted to a signal generating circuit 2 that generates the start signal and in doing so incorporates the delay signal into the start signal.

Figure 6B:
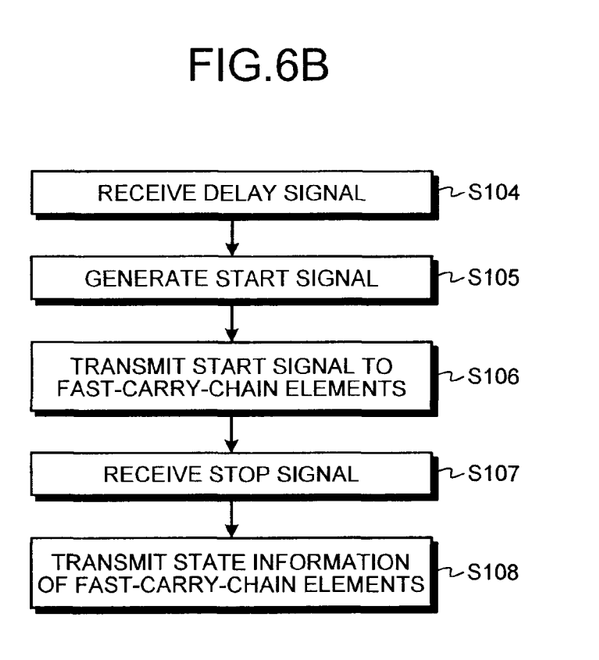
FIG. 6B is a flow diagram illustrating a process of implementing a time-to-digital conversion after the determined delay has been incorporated.

FIG. 6B illustrates a process of implementing a time-to-digital conversion after the determined delay has been incorporated according to one embodiment. For example, the processing in the flowchart is performed controlled by the control unit 540 (see FIG. 5) or the CPU 1004 (see FIG. E).

In step S104, the delay signal is received at the signal generating circuit.

In step S105, a start signal incorporating the delay signal into the start signal is generated by the signal generating circuit 2.

In step S106, the generated start signal is transmitted to the chain of fast-carry-chain elements 10A-n via input 5.

In step S107, a stop signal is received at each of the plurality of fast-carry-chain elements 10A-n.

In step S108, state information for each of the fast-carry-chain elements is transmitted to a time determining circuit that determines the time at which an event occurred based on the state information.

Figure 7:
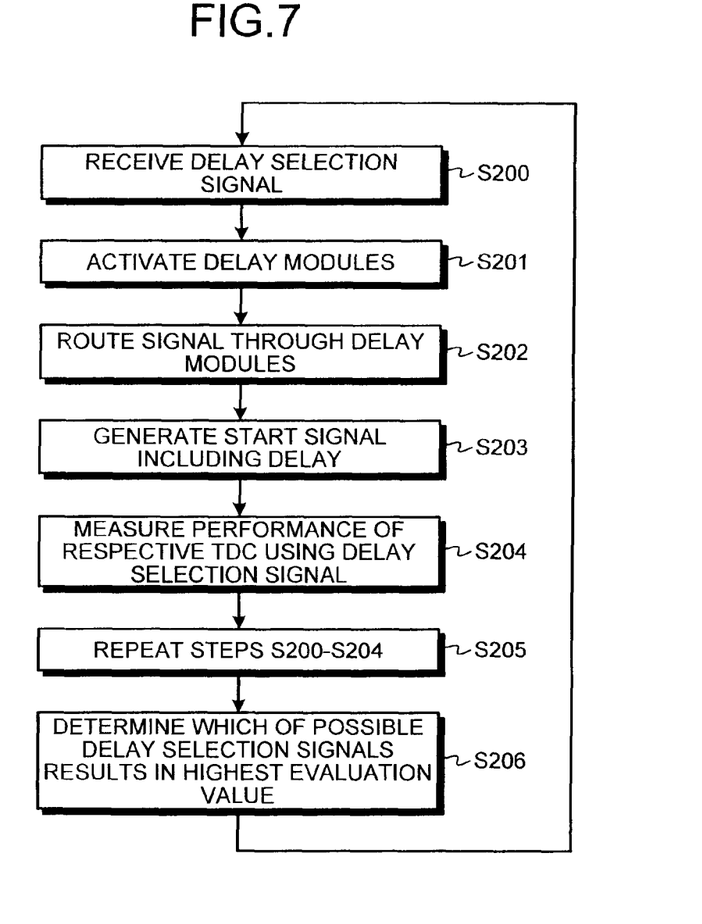
FIG. 7 is a flow diagram illustrating the process for determining the optimal delay according to one embodiment.

FIG. 7 illustrates a method of calibrating a metastable ring oscillator chain-based TDC. For example, the processing in the flowchart is performed controlled by the control unit 540 (see FIG. 5) or the CPU 1004 (see FIG. 8).

In step S200, a delay selection signal (corresponding to enable signals 8A-n) is received indicating a determination of an amount of delay to incorporate into the start signal.

In step S201, one or more delay modules is activated based on the delay selection signal, the one or more delay modules selected from the chain of fast-chain-carry elements 10A-n.

In step S202, delay is generated by routing a delay signal through at least one of the one or more delay modules that has been activated by the delay selection signal.

In step S203, the delay signal is transmitted to a signal generating circuit 2 that generates the start signal and in doing so incorporates the delay signal into the start signal.

In step S204, the performance of the respective TDC is measured using the delay selection signal to obtain an evaluation value for the delay selection signal. The delay selection signal or group of selection signals are compared with an output result of the TDC system in order to determine an evaluation value which for the delay selection signal(s). The evaluation values are recorded in association with the delay selection signal(s).

In step S205, steps S201-S204 are repeated for each possible delay selection signal or combination to obtain a plurality of evaluation values with one evaluation value for each possible delay selection signal or group of selection signals. Each of these evaluation values is recorded in association with the respective signal or signals.

In step S206, a determination is made regarding which of the possible delay selection signal(s) results in the highest evaluation value. As is described above, the various delay configurations can be evaluated using a technique in which pairs of start-stop signals of known timing (for example from a function generator) are injected into the system. For each configuration of enable0_n and enable1_n pairs as described above, a histogram of the times between the start and stop, as measured by the TDC in a given configuration, is generated. This generation may be performed using a microprocessor implemented histogram generation program. A distribution of timing values is derived from the histogram. The distribution is analyzed and the quality of the configuration is based on a metric calculated in the distribution. Examples of the metric include but are not limited to the standard deviation or the Full Width Half Max (FWHM). The selection signal or signals determined to provide the optimal delay can then be used to provide the optimal delay for the TDC process.

Certain portions of the processing, such as the optimization and the generation of delay selection signal, can be implemented or aided by using some form of computer having at least one microprocessor or by using a processor. As one of ordinary skill in the art would recognize, the computer processor can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the computer processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OSX and other operating systems known to those skilled in the art.

Figure 8:
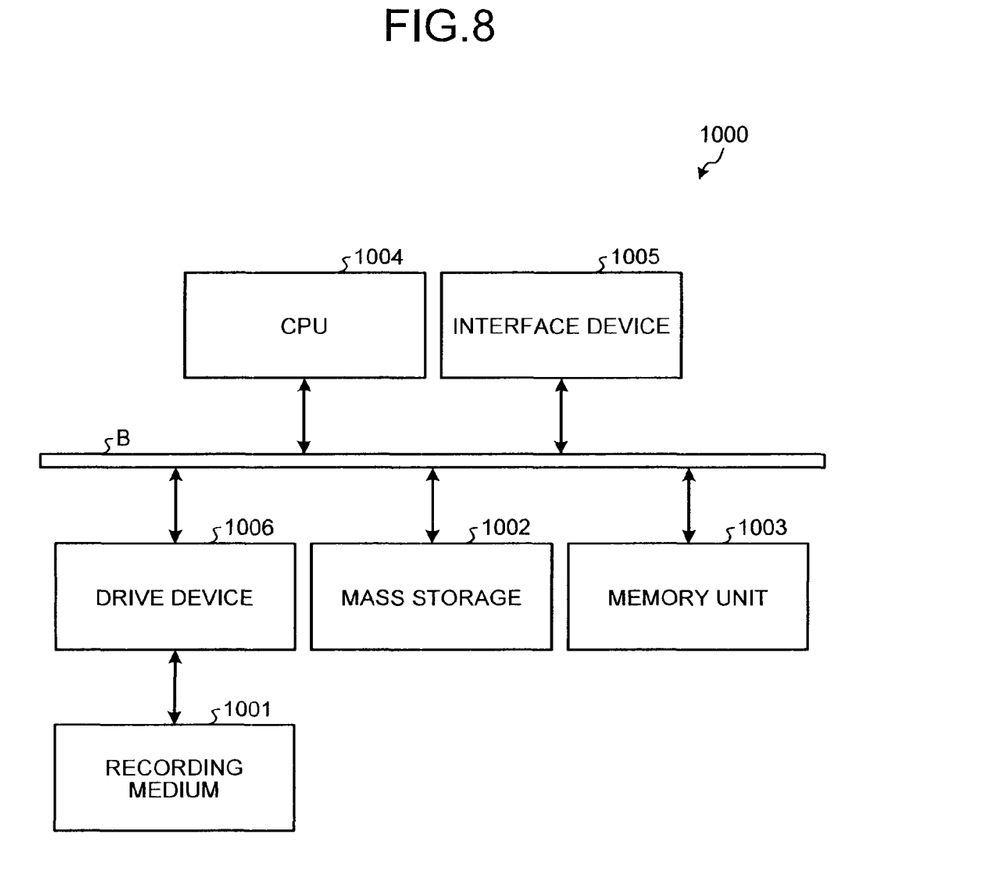
FIG. 8 illustrates a computing device according to one embodiment.

In addition, certain features of the embodiments can be implemented using a computer based system (FIG. 8). The computer 1000 includes a bus B or other communication mechanism for communicating information, and a processor/CPU 1004 coupled with the bus B for processing the information. The computer 1000 also includes a main memory/memory unit 1003, such as a random access memory (RAM) or other dynamic storage device (e.g., dynamic RAM (DRAM), static RAM (SRAM), and synchronous DRAM (SDRAM)), coupled to the bus B for storing information and instructions to be executed by processor/CPU 1004. In addition, the memory unit 1003 may be used for storing temporary variables or other intermediate information during the execution of instructions by the CPU 1004. The computer 1000 may also further include a read only memory (ROM) or other static storage device (e.g., programmable ROM (PROM), erasable PROM (EPROM), and electrically erasable PROM (EEPROM)) coupled to the bus B for storing static information and instructions for the CPU 1004.

The computer 1000 may also include a disk controller coupled to the bus B to control one or more storage devices for storing information and instructions, such as a mass storage 1002, and a drive device 1006 (e.g., floppy disk drive, read-only compact disc drive, read/write compact disc drive, compact disc jukebox, tape drive, and removable magneto-optical drive). The storage devices may be added to the computer 1000 using an appropriate device interface (e.g., small computer system interface (SCSI), integrated device electronics (IDE), enhanced-IDE (E-IDE), direct memory access (DMA), or ultra-DMA).

The computer 1000 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer 1000 may also include a display controller coupled to the bus B to control a display, such as a cathode ray tube (CRT), for displaying information to a computer user. The computer system includes input devices, such as a keyboard and a pointing device, for interacting with a computer user and providing information to the processor. The pointing device, for example, may be a mouse, a trackball, or a pointing stick for communicating direction information and command selections to the processor and for controlling cursor movement on the display. In addition, a printer may provide printed listings of data stored and/or generated by the computer system.

The computer 1000 performs at least a portion of the processing steps of the present embodiment in response to the CPU 1004 executing one or more sequences of one or more instructions contained in a memory, such as the memory unit 1003. Such instructions may be read into the memory unit from another computer readable medium, such as the mass storage 1002 or a removable media 1001. One or more processors in a multi-processing arrangement may also be employed to execute the sequences of instructions contained in the memory unit 1003. In alternative embodiments, hard-wired circuitry may be used in place of or in combination with software instructions. Thus, embodiments are not limited to any specific combination of hardware circuitry and software.

As stated above, the computer 1000 includes at least one removable media 1001 or memory for holding instructions programmed according to the teachings of the present embodiment and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other medium from which a computer can read.

Stored on any one or on a combination of computer readable media, the present embodiment includes software for controlling the main processing unit 1004, for driving a device or devices for implementing the present embodiment, and for enabling the main processing unit 1004 to interact with a human user. Such software may include, but is not limited to, device drivers, operating systems, development tools, and applications software. Such computer readable media further includes the computer program product of the present embodiment for performing all or a portion (if processing is distributed) of the processing performed in implementing the present embodiment.

The computer code elements on the medium of the present embodiment may be any interpretable or executable code mechanism, including but not limited to scripts, interpretable programs, dynamic link libraries (DLLs), Java classes, and complete executable programs. Moreover, parts of the processing of the present embodiment may be distributed for better performance, reliability, and/or cost.

The term "computer readable medium" as used herein refers to any medium that participates in providing instructions to the CPU 1004 for execution. A computer readable medium may take many forms, including but not limited to, non-volatile media, and volatile media. Non-volatile media includes, for example, optical, magnetic disks, and magneto-optical disks, such as the mass storage 1002 or the removable media 1001. Volatile media includes dynamic memory, such as the memory unit 1003.

Various forms of computer readable media may be involved in carrying out one or more sequences of one or more instructions to the CPU 1004 for execution. For example, the instructions may initially be carried on a magnetic disk of a remote computer. An input coupled to the bus B can receive the data and place the data on the bus B. The bus B carries the data to the memory unit 1003, from which the CPU 1004 retrieves and executes the instructions. The instructions received by the memory unit 1003 may optionally be stored on the mass storage 1002 either before or after execution by the CPU 1004.

The computer 1000 also includes a communication interface 1005 coupled to the bus B. The communication interface 1004 provides a two-way data communication coupling to a network that is connected to, for example, a local area network (LAN), or to another communications network such as the Internet. For example, the communication interface 1005 may be a network interface card to attach to any packet switched LAN. As another example, the communication interface 1005 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1005 sends and receives electrical, electromagnetic or optical signals that carry digital data streams representing various types of information.

The network typically provides data communication through one or more networks to other data devices. For example, the network may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). Moreover, the network may provide a connection to a mobile device such as a personal digital assistant (PDA) laptop computer, or cellular telephone.

In the above descriptions, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions may be executed out of order from that shown or discussed, including substantially concurrently or in reverse order, depending upon the functionality involved, as would be understood by those skilled in the art.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

What is claimed is:

1. A nuclear medicine imaging apparatus, comprising:
a counting information collection unit implemented by circuitry that collects counting information including detection time of radiation in detecting the radiation emitted from a nuclide administered to a subject; and
a reconstruction unit implemented by circuitry that reconstructs a nuclear medicine image based on the counting information, wherein
the counting information collection unit comprises:
a signal generating circuit configured to generate a start signal of a time-to-digital circuit (TDC) that measures the detection time of the radiation;
a plurality of carry elements connected as a chain, each of the carry elements having an input to receive a stop signal; and
a delay chain circuit including one or more delay modules selected from the plurality of carry elements, at least one feedback line connected between at least one of the delay modules and the signal generating circuit, and a plurality of enable inputs each provided in a respective one of the delay modules,
wherein the delay chain circuit is configured to generate an amount of delay based on a delay selection signal that is received at the enable inputs and that selects the amount of delay, and is configured to provide the selected amount of delay to the signal generating circuit, which is further configured to incorporate the delay into the start signal.

2. The nuclear medicine imaging apparatus according to claim 1, wherein the signal generating circuit is further configured to incorporate the delay between edges in the start signal.

3. The nuclear medicine imaging apparatus according to claim 1, further comprising:
a time determining circuit configured to determine the time at which an event occurred based on state information transferred from each of the carry elements.

4. The nuclear medicine imaging apparatus according to claim 1, wherein the delay selection signal provides an indication to each delay module whether the respective delay module is activated to generate delay.

5. The nuclear medicine imaging apparatus according to claim 1, wherein the signal generating circuit includes at least one flip-flop.

6. The nuclear medicine imaging apparatus according to claim 1, wherein each of the delay modules includes at least one hardware based look up table (LUT).

7. The nuclear medicine imaging apparatus according to claim 1, wherein each of the delay modules includes at least one flip-flop.

8. The nuclear medicine imaging apparatus according to claim 1, wherein the delay selection signal is determined by user input.

9. The nuclear medicine imaging apparatus according to claim 1, wherein the delay selection signal is determined by an algorithm which determines the optimal propagation delay for the TDC.

10. The nuclear medicine imaging apparatus according to claim 1, wherein the TDC is implemented on field programmable gate arrays (FPGAs).

* * * * *